(12) United States Patent
Maury et al.

(10) Patent No.: US 11,618,721 B2
(45) Date of Patent: Apr. 4, 2023

(54) METHOD FOR ISOMERISING DEHYDRATION OF A NON-LINEAR PRIMARY MONOALCOHOL ON A QUADRILOBED IRON ZEOLITE CATALYST

(71) Applicants: IFP Energies nouvelles, Rueil-Malmaison (FR); TOTAL RESEARCH & TECHNOLOGY FELUY, Seneffe (BE)

(72) Inventors: Sylvie Maury, Rueil-Malmaison (FR); Vincent Coupard, Rueil-Malmaison (FR); Delphine Bazer-Bachi, Rueil-Malmaison (FR); Joseph Lopez, Saint Julien les Rosiers (FR); Nikolai Nesterenko, Nivelles (BE); Guillaume Duplan, Saint Julien les Rosiers (FR); Colin Dupont, Brussels (BE)

(73) Assignees: IFP Energies Nouvelles, Rueil-Malmaison (FR); TOTAL RESEARCH & TECHNOLOGY FELUY, Seneffe (BE)

( * ) Notice: Subject to any disclaimer, the term of this patent is extended or adjusted under 35 U.S.C. 154(b) by 131 days.

(21) Appl. No.: 17/050,155

(22) PCT Filed: Apr. 4, 2019

(86) PCT No.: PCT/EP2019/058454
§ 371 (c)(1),
(2) Date: Oct. 23, 2020

(87) PCT Pub. No.: WO2019/206591
PCT Pub. Date: Oct. 31, 2019

(65) Prior Publication Data
US 2021/0078919 A1 Mar. 18, 2021

(30) Foreign Application Priority Data
Apr. 25, 2018 (FR) ...................... 1853627

(51) Int. Cl.
| | | |
|---|---|---|
| *B01J 29/06* | (2006.01) |
| *C07C 1/24* | (2006.01) |
| *B01J 21/08* | (2006.01) |
| *B01J 29/65* | (2006.01) |
| *B01J 35/02* | (2006.01) |
| *B01J 35/10* | (2006.01) |
| *B01J 37/00* | (2006.01) |
| *B01J 37/04* | (2006.01) |
| *B01J 37/08* | (2006.01) |
| *B01J 37/10* | (2006.01) |
| *C07C 5/27* | (2006.01) |

(52) U.S. Cl.
CPC ............ *C07C 1/24* (2013.01); *B01J 21/08* (2013.01); *B01J 29/65* (2013.01); *B01J 35/026* (2013.01); *B01J 35/1019* (2013.01); *B01J 35/1042* (2013.01); *B01J 35/1061* (2013.01); *B01J 35/1076* (2013.01); *B01J 35/1095* (2013.01); *B01J 37/0009* (2013.01); *B01J 37/04* (2013.01); *B01J 37/082* (2013.01); *B01J 37/10* (2013.01); *C07C 5/2775* (2013.01); *B01J 2229/36* (2013.01); *C07C 2521/08* (2013.01); *C07C 2529/65* (2013.01)

(58) Field of Classification Search
CPC ........ B01J 21/08; B01J 29/65; B01J 29/7026; B01J 2229/42; B01J 35/026; B01J 35/1019; B01J 35/1042; B01J 35/1047; B01J 35/1095; B01J 35/1061; B01J 35/1066; B01J 35/1071; B01J 35/1076; B01J 37/0009; B01J 37/082; B01J 37/10; B01J 2219/30296; B01J 35/1033; B01J 35/1052; B01J 35/1004; B01J 37/04; C07C 5/2775; C07C 2521/08; C07C 2529/65; C07C 2529/70; C07C 1/24; C10G 3/49; C10G 2400/20; C10G 2400/22
USPC .............. 502/60, 63, 64, 69, 71, 77, 527.23, 502/527.24; 585/638, 639, 640; 208/133, 134, 135, 141
See application file for complete search history.

(56) References Cited

U.S. PATENT DOCUMENTS

2017/0341996 A1\* 11/2017 Vivien .................. C07C 5/2775
2019/0270687 A1 9/2019 Maury et al.

FOREIGN PATENT DOCUMENTS

| WO | 16046242 A1 | 3/2016 |
| WO | 18087032 A1 | 5/2018 |
| WO | 18087033 A1 | 5/2018 |

OTHER PUBLICATIONS

Baerlocher et al. "Atlas of Zeolite Framework Types", Fifth Revised Edition, p. 141, 2001.\*

(Continued)

*Primary Examiner* — Elizabeth D Wood
(74) *Attorney, Agent, or Firm* — Millen White Zelano and Branigan, PC; Csaba Henter

(57) ABSTRACT

A method for isomerising dehydration in the presence of a specific catalyst, to produce at least one alkene, carried out on a feedstock containing a non-linear primary monoalcohol, where the catalyst includes a zeolite having a series of 8MR channels and a binder having certain pore volume, which catalyst is multilobe-shaped and has characteristics including certain average mesopore volume Vm, and mesopores having a certain diameter, an average certain macropore volume VM, the macropores having a certain diameter, and certain average micropore volume Vµ, the micropores having a certain diameter, and the catalyst has a certain exposed geometric area.

22 Claims, No Drawings

(56) References Cited

OTHER PUBLICATIONS

International Search Report PCT/EP2019/058454 dated Jun. 5, 2019 (pp. 1-2).

* cited by examiner

METHOD FOR ISOMERISING DEHYDRATION OF A NON-LINEAR PRIMARY MONOALCOHOL ON A QUADRILOBED IRON ZEOLITE CATALYST

TECHNICAL FIELD OF THE INVENTION

The present invention relates to a catalyst and an improved process for producing alkenes starting from a feedstock comprising, alone or in a mixture, a primary monoalcohol of formula R—$CH_2$—OH in which R is a nonlinear alkyl radical of general formula $C_nH_{2n+1}$, where n is an integer between 3 and 20 (such as isobutanol). This feedstock may be obtained by chemical processes or by fermentation processes. This process employs a catalyst based on a zeolite comprising at least one series of channels in which the aperture is defined by a ring of 8 oxygen atoms (8 MR), this catalyst having optimized morphological and textural characteristics which enable it to operate in the absence of precoking.

The alkenes obtained, in particular isobutene, 1-butene and 2-butenes, are of great value in the field of the petrochemical industry and of organic synthesis.

PRIOR ART

Isobutene is a key molecule in petrochemistry particularly for the synthesis of gasolene additives such as ETBE and MTBE. The vast majority of the publications relate to the production of isobutene from linear butanols, these being more easily produced by conventional fermentation pathways (ABE) than isobutanol. Recent developments have, however, made it possible to greatly improve the fermentation yields of isobutanol, making this feedstock accessible and available at an attractive cost.

Document WO-2009/079213 describes the sequencing of dehydration reactions of biobased alcohols (C2-C7) over an acidic catalyst to form olefins, followed by oligomerization of the olefins over an acidic oligomerization catalyst (zeolite or alumina). The target application is the preparation of kerosene (jet fuel).

Document EP-2348005 belonging to Total describes the dehydration of alcohols containing from 2 to 10 carbon atoms to the corresponding olefin over an FER zeolite catalyst with an Si/Al atomic ratio of less than 100. The mass (or weight) hourly space velocity (WHSV) relative to the alcohol is at least 4 $h^{-1}$ and the temperature is from 320 to 600° C. The catalyst may take the form of pellets, extrudates, spheres, atomized powder or multilobes.

Document WO-2011/089235 describes other zeolite structural types all belonging to the family of the zeolites having an average channel size (10MR), with an Si/Al molar ratio of less than 100. The zeolites may be modified by various aftertreatments. The catalyst is used for dehydrating alcohols containing from 2 to 10 carbon atoms to the corresponding olefin.

Document WO-2011/113834 belonging to Total describes the simultaneous dehydration and skeletal isomerization of isobutanol in the presence of crystalline silicate catalysts having an average channel size (10MR), which are optionally dealuminated and optionally phosphorus-modified, of the FER, MWW, EUO, MFS, ZSM-48, MTT, MFI, MEL or TON group having an Si/Al ratio of more than 10, or of silicoaluminophosphate molecular sieves of the AEL group, or silica-, zirconia-, titania- or fluoro-alumina. The WHSV relative to the alcohol is at least 1 $h^{-1}$ and the temperature is from 200 to 600° C. The maximum proportion of n-butenes attained in the butenes (isobutene plus butenes) is 58.4% at 375° C. with a high WHSV (12.6 $h^{-1}$) over an FER zeolite powder of Si/Al 33.

As in the preceding references, the catalyst may take the form of pellets, extrudates, spheres, atomized powder or multilobes.

The dehydration of C4 alcohols over acid solids is generally accompanied by the positional isomerization of the alkene formed. These two reactions are actually concomitant, since the positional isomerization of the double bond of the alkene is as fast as the dehydration reaction of the C4 monoalcohol. In the case of isobutanol, the isobutene formed during the reactions is readily protonated (formation of a tertiary carbocation) and is subsequently able to undergo secondary reactions, particularly dimerization reactions, and then cyclization, which carry the risk of giving rise to the formation of unwanted secondary products.

The dehydration of n-butanol followed by the skeletal isomerization of the resulting n-butenes was described by Chadwik et al. (Applied Catalysis 2011, issue 1-2, volume 403, pp. 1-11) over various zeolitic catalysts. The form of the catalysts is that of granules of 0.5-0.8 mm, obtained after grinding of zeolite pellets. The authors report substantial instability of ferrierite in the presence of the water formed during the dehydration reaction, and a deterioration in this catalytic performances over time (drop in the yield of butenes).

However, Kotsarenko et al., Kin. Katal. 24, 877 (1983), describes, in the specific case of the simultaneous dehydration and skeletal isomerization of isobutanol over nonzeolitic solids, a mechanism in which an intermediate primary carbocation species formed by dehydration at an acidic site on the alcohol undergoes rearrangement via a molecular rearrangement reaction ("methyl shift") to form a secondary carbocation and promote the formation of linear butenes. The most highly performing catalysts are disorganized mixed oxides based on alumina and silica, with an alumina content of less than 5%. The maximum proportion of n-butenes reached in the butenes is 32.7% at temperatures of between 275 and 350° C.

The present invention relates to a process for converting a nonlinear primary monoalcohol into alkene, using a zeolitic catalyst.

An objective of the invention is to enhance the performances of the conversion process and of the catalyst. A more specific objective of the invention is to optimize the selectivity for alkenes and especially the selectivity for linear alkenes. The invention also aims to improve the stability of the catalyst.

SUMMARY OF THE INVENTION

The invention relates to a process for isomerizing dehydration of a feedstock comprising, alone or in a mixture, a primary monoalcohol of formula R—$CH_2$—OH, in which R is a nonlinear alkyl radical of general formula $C_nH_{2n+1}$ where n is an integer of between 3 and 20, said process comprising a step of isomerizing dehydration operated in the gas phase at a weighted average temperature of between 250 and 460° C., at a pressure of between 0.2 MPa and 1 MPa, at a weight hourly space velocity (WWH) of between 1 and 25 $h^{-1}$, in the presence of a catalyst comprising at least one zeolite and at least one binder, in which the amount by weight Tz of zeolite is 55-90 wt % relative to the total weight of said catalyst and in which said zeolite has at least one series of channels with an aperture of 8 oxygen atoms (8MR), said binder having a pore volume of between 0.5 and 0.9 ml/g, the catalyst being multilobate and having:
- an average mesopore volume Vm centered at plus or minus 20% around the value defined by the formula Vm=−0.004Tz+0.505, the mesopores having a diameter of 3.6 nm to 50 nm,
- an average macropore volume VM centered at plus or minus 20% around the value defined by the formula VM=0.0101Tz−0.5375, the macropores having a diameter of more than 50 nm and less than 7000 nm,
- an average micropore volume Vμ centered at plus or minus 20% around the value defined by the formula Vμ=0.0014Tz−0.0006, the micropores having a diameter of less than 2 nm,
- and, in the formulas, Tz is expressed in wt % and the pore volumes are expressed in ml/g,
- an exposed geometric area of 2700 to 11 000 $m^2/m^3$ of catalyst bed volume.

The present invention likewise relates to a catalyst comprising at least one zeolite and at least one binder, in which the amount by weight Tz of zeolite is 50-90 wt %, said binder having a pore volume of between 0.5 and 0.9 ml/g, said catalyst comprising at least one zeolite having at least one series of channels having an aperture of 8 oxygen atoms (8MR), the catalyst being multilobate and having
- an average mesopore volume Vm centered at plus or minus 20% around the value defined by the formula Vm=−0.004Tz+0.505, the mesopores having a diameter of 3.6 nm to 50 nm,
- an average macropore volume VM centered at plus or minus 20% around the value defined by the formula VM=0.0101Tz−0.5375, the macropores having a diameter of more than 50 nm and less than 7000 nm,
- an average micropore volume Vμ centered at plus or minus 20% around the value defined by the formula Vμ=0.0014Tz−0.0006, the micropores having a diameter of less than 2 nm,
- and, in the formulas, Tz is expressed in wt % and the pore volumes are expressed in ml/g,
- an exposed geometric area of 2700 to 11000 $m^2/m^3$ of catalyst bed volume.

The inventors have observed, surprisingly, that a catalyst of this kind having the specific morphological features (geometric shape) and textural features (porosities) according to the invention allows enhanced performances to be obtained. More particularly, a catalyst of this kind allows a much greater proportion of linear alkenes to be obtained in the alkenes fraction, relative to the anticipated value at the thermodynamic equilibrium.

Moreover, the catalyst according to the invention undergoes little deactivation relative to the prior-art catalysts, so especially improving the conversion performances over time.

DESCRIPTION OF THE INVENTION

According to the invention, the pore volume of the binder corresponds to the total pore volume of the solid used as binder. It is measured by analyzing the nitrogen adsorption isotherm, as detailed hereinafter.

According to the present invention, the expression "between . . . and . . . " means that the limiting values of the interval are included in the range of values which is described. If such were not the case and if the limiting values were not included in the range described, such a clarification will be given by the present invention.

The invention relates to a process for isomerizing dehydration of a feedstock comprising, alone or in a mixture, a primary monoalcohol of formula R—$CH_2$—OH, in which R is a nonlinear alkyl radical of general formula $C_nH_{2n+1}$ where n is an integer of between 3 and 20 (such as isobutanol), said process comprising a step of isomerizing dehydration operated in the gas phase at a weighted average temperature of between 250 and 460° C., at a pressure of between 0.2 MPa and 1 MPa, at a weight hourly space velocity (WWH) of between 1 and 25 $h^{-1}$, in the presence of a catalyst comprising at least one zeolite and at least one binder, in which the amount by weight Tz of zeolite is 55-90 wt % relative to the total weight of said catalyst and in which said zeolite has at least one series of channels with an aperture of 8 oxygen atoms (8MR), said binder having a pore volume of between 0.5 and 0.9 ml/g, the catalyst being multilobate and having:
- an average mesopore volume Vm centered at plus or minus 20% around the value defined by the formula Vm=−0.004Tz+0.505, the mesopores having a diameter of 3.6 nm to 50 nm,
- an average macropore volume VM centered at plus or minus 20% around the value defined by the formula VM=0.0101Tz−0.5375, the macropores having a diameter of more than 50 nm and less than 7000 nm,
- an average micropore volume Vμ centered at plus or minus 20% around the value defined by the formula Vμ=0.0014Tz−0.0006, the micropores having a diameter of less than 2 nm,
- and, in the formulas, Tz is expressed in wt % and the pore volumes are expressed in ml/g,
- an exposed geometric area of 2700 to 11 000 $m^2/m^3$ of catalyst bed volume.

The mesopore and macropore volumes of the catalyst, which correspond respectively to the volume occupied by the mesopores having a diameter of 3.6 nm to 50 nm and the volume occupied by the macropores having a diameter of more than 50 nm and less than 7000 nm, are measured by mercury intrusion porosimetry according to the standard ASTM D4284-83 at a maximum pressure of 4000 bar, using a surface tension of 484 dyn/cm and a contact angle of 141°. The wetting angle was taken as equal to 110°, following the recommendations in the work "Techniques de l'ingénieur, traité analyse et caractérisation", 1050, by J. Charpin and B. Rasneur. In order to obtain better precision, the value of the mercury volume in ml/g that is given in the text which follows corresponds to the value of the total mercury volume in ml/g measured on the sample minus the value of the mercury volume in ml/g measured on the same sample for a pressure corresponding to 30 psi (approximately 2 bar).

The micropore volume, especially of the catalyst formed, is measured by analyzing the nitrogen adsorption isotherm. The micropore volume of the catalyst according to the invention corresponds to the volume occupied by the pores with a diameter less than 2 nm.

The nitrogen adsorption isotherm analysis, which corresponds to the physical adsorption of nitrogen molecules in the porosity of said solid by a progressive increase in the pressure, at constant temperature, provides information on the textural characteristics (pore diameter, type of porosity, specific surface area) of the zeolitic solid in the catalyst used according to the invention. More particularly, it provides access to the specific surface area, to the micropore volume and to the pore distribution of said solid.

The specific surface area refers to the BET specific area ($S_{BET}$ in $m^2/g$) determined by nitrogen adsorption in accordance with the standard ASTM D-3663-78, drawn up on the basis of the BRUNAUER-EMMETT-TELLER method described in the journal "*The Journal of American Society*", 1938, 60, 309.

The exposed geometric surface area can be calculated by the skilled person, and is the ratio between the external geometric surface area (which is not the BET specific surface area) of the catalyst and the volume of catalyst charged to the reactor.

The formulas used for calculating the external geometric surface area are as follows:

$$\text{-for a trilobe: } L = 1000(1 - Tv)\left[\frac{2}{H} + 10\frac{\pi}{\left(D\left(\frac{\sqrt{3}}{2} + \frac{5\pi}{4}\right)\right)}\right]$$

$$\text{-for a quadrilobe: } L = 1000(1 - Tv)\left[\frac{3\frac{\sqrt{2}}{2}\pi\left(\frac{D}{2}\right)H + \left(\frac{3\pi+4}{4}\right)\left(\frac{D}{2}\right)^2}{V}\right]$$

$$\text{with } V = \left(\frac{3\pi+4}{8}\right)\left(\frac{D}{2}\right)^2 H$$

$$\text{-for a cylinder: } L = 1000(1 - Tv)\left[2\left(\frac{2}{D} + \frac{1}{H}\right)\right]$$

with
L=external geometric surface area/catalyst bed volume, $m^2/m^3$
D=external (circumscribed) diameter, mm
H=extruded length, mm
Tv=void fraction in the catalyst bed (fraction)
V=calculated volume of an extrudate The external geometric surface (area) corresponds to the geometric surface area of the catalyst bed, expressed relative to the volume occupied by the same catalyst bed. When the catalyst is charged in a reactor, this geometric surface area corresponds to the external geometric surface (area) relative to the volume of the catalyst bed in the reactor.

The packing density of the catalyst, when charged to a reactor, for example, is measured (ASTM-D-7481-09) for particles ranging up to 3.5 mm. The void level in the catalyst bed is deduced from this, by referring, for example, to "Catalyse de contact: conception, préparation et mise en œuvre des catalyseurs industriels", J. F. Le Page, page 209.

The process according to the invention provides access, at the end of the reaction step, to an effluent comprising a proportion of linear alkenes above that expected when taking into account the thermodynamic equilibrium between the alkenes at the reactor outlet temperature. This results in excellent conversion of the alcohol (greater than 97 mol %) and very good selectivity for total alkenes (greater than 97 mol %).

Feedstock

In accordance with the invention, the feedstock treated in the process according to the invention is a feedstock comprising, alone or in a mixture, a primary monoalcohol of formula R—CH$_2$—OH in which R is a nonlinear alkyl radical of general formula $C_nH_{2n+1}$, where n is an integer between 3 and 20 (such as isobutanol).

In the rest of the specification, the term alkyl denotes a hydrocarbon compound of general formula $C_nH_{2n+1}$ where n is an integer between 3 and 20, preferably between 3 and 10, more preferably between 3 and 5.

The feedstock preferably comprises from 40 to 100 wt % of said primary monoalcohol.

As the primary monoalcohol according to the invention, mention may be made of isobutanol, 2-methylbutan-1-ol, 2,2-dimethylpropan-1-ol, 2-methylpentan-1-ol, 2,2-dimethylbutan-1-ol and 2-ethylbutan-1-ol. They may be alone or in a mixture.

Said primary monoalcohol is preferentially isobutanol or 2-methyl-1-butanol, taken alone or as a mixture. Very preferentially, said alcohol is essentially isobutanol; preferably the only primary monoalcohol is isobutanol.

Said feedstock may originate from chemical or biochemical processes, for example fermentation processes. In particular, this feedstock may be derived from lignocellulosic biomass fermentation processes.

Said feedstock may contain water, in particular up to 60% of water. It may also comprise impurities of mineral type (such as Na, Ca, P, Al, Si, K, SO$_4$) and of organic type (such as methanol, ethanol, n-butanol, aldehydes, ketones and the corresponding acids, for example furanic, acetic or isobutyric acid).

Process

The process according to the invention comprises a step of isomerizing dehydration performed in the gas phase, at a weighted average temperature of between 250 and 460° C., preferably between 250 and 400° C., or even 250-375° C., at a pressure of between 0.2 MPa and 1 MPa, at a weight hourly space velocity (WWH) of between 1 and 25 h$^{-1}$, preferably 1 and 20 h$^{-1}$, in the presence of the catalyst according to the invention. Said catalyst is positioned in one or more fixed beds, which may be operated in upflow, downflow or radial flow mode.

WWH refers to "weight per weight per hour", and corresponds to the weight hourly space velocity. Weight hourly space velocity (WWH) refers to the mass flow of primary monoalcohol in the feedstock, at the reactor entry, divided by the mass of catalyst in said reactor. This concept is also sometimes denoted under the acronym WHSV or "weight hourly space velocity".

The term "weighted average temperature" (denoted by WAT) means the average temperature in the catalytic bed, the bed being all of the beds present in the reactor, in which beds the catalytic reaction takes place, calculated along the axis of flow through said bed. Namely a bed of length L and of surface area S, the reactive mixture flowing along the longitudinal axis x of this bed, the inlet into the catalytic bed forming the origin of the axis (x=0), the weighted average temperature, denoted by WAT, is expressed according to the following formula:

$$WAT = \frac{1}{L}\int_0^L T(x)dx$$

Since the reaction is endothermic and the reactor operates either in isothermal mode, or in adiabatic mode, the weighted average temperature will be representative of the reaction temperature.

The reaction takes place in one or more reactors and each reactor is operated under independent or identical conditions. The operating conditions for each reactor (pressure, temperature WAT, residence time) are selected depending on the feedstock conversion objective and on the desired selectivity for linear olefins. The WAT of each of the reactors is adjusted to a value between 275° C. and 460° C. Thus, in the remainder of the description, the term "the reactor" denotes both the reactor of this step when this step comprises only one reactor, and each of the reactors of this step, when this step comprises more than one reactor. Said catalyst is positioned in one or more fixed beds, which may be operated in upflow, downflow or radial flow mode.

Since the dehydration reaction is endothermic, the heat input is achieved by any heating means known to a person skilled in the art.

Before coming into contact with the feedstock to be treated, the catalyst is activated by any means known to a person skilled in the art, for example by heat treatment in air.

Catalyst

In accordance with the invention, the catalyst employed comprises at least one zeolite, said zeolite having at least one series of channels, in which the aperture is defined by a ring of 8 oxygen atoms (8MR), as defined in the classification "Atlas of Zeolite Structure Types", Ch. Baerlocher, L. B. McCusker, D. H. Olson, 6th Edition, Elsevier, 2007, Elsevier".

This zeolite is shaped with a binder, preferably a silicic binder, with a multilobate geometry, preferably trilobate or quadrilobate, and the resulting material has adapted pore volumes.

A catalyst referred to as multilobate means a catalyst having at least 3 lobes. It may advantageously be a trilobe or a quadrilobe, preferably a quadrilobe.

A quadrilobate catalyst has 4 lobes and the cross section is generally within a circumscribed circle with a diameter of 1 mm to 9 mm, or in an oval whose principal axis is from 2 mm to 9 mm and whose secondary axis is from 1.2 mm to 7 mm.

For a trilobate catalyst, the cross section is generally in a circumscribed circle with a diameter of 1.6 mm or in an oval whose principal axis is from 1.2 to 2 mm and whose secondary axis is from 1.2 to 1.6 mm.

The catalyst is preferably quadrilobate and has a diameter relative to the circumscribed circle of between 1 mm and 9 mm, preferably between 1 mm and 5 mm, more preferably between 1.2 and 3 mm, and more preferably still between 1.2 and 2 mm.

According to one particular embodiment, said zeolite may also advantageously contain at least one series of channels, the pore opening of which is defined by a ring containing 10 oxygen atoms (10 MR).

Said zeolite is advantageously selected from zeolites having 8 and 10MR channels such as zeolites of FER and MFS structural type, taken alone or as a mixture. The zeolite is more advantageously selected, in the FER type, from ferrierite, FU-9, ISI-6, NU-23, ZSM-35 zeolites, and for the MFS type it is the ZSM-57 zeolite, taken alone or as a mixture. Said zeolite is very advantageously of FER type and preferably is ferrierite. Preferably, said zeolite consists of ferrierite.

The ferrierite preferably has an Si/Al molar ratio of 8 to 70, preferably 15 to 70, and preferably selected between 20 and 50 or between 10 and 50.

The amount of said zeolite in the catalyst, denoted Tz, is 55-90 wt %, preferably between 60 and 80 wt % relative to the total weight of the catalyst.

The zeolite is shaped with said binder, which is advantageously inert. This is because, since the zeolite cannot be used industrially in powder form, the binder provides the final solid with increased resistance in the presence of water. The binder also makes it possible to use the catalyst thus constituted in a fixed bed in a reactor, without an excessive pressure loss.

The binder has a pore volume of between 0.5 and 0.9 ml/g, preferably of between 0.6 and 0.8 ml/g. The pore volume of the binder corresponds to the total pore volume of said binder, in particular to the volume occupied by the meso- and micropores present in the solid binder. It is measured by analyzing the nitrogen adsorption isotherm. When the binder consists of a plurality of sources (a number i of sources, i being an integer greater than or equal to 2), the pore volume of the binder according to the invention is the total pore volume resulting from the sum of the pore volumes Vi of the various sources weighted by the weight fractions (Xi) of said i sources constituting the binder.

Thus: $Vp(binder)=\Sigma Xi \times Vi$ with Vp(binder) being the pore volume of the binder
Xi being the weight fraction of the binder source i relative to the total weight of the binder, and
Vi being the (total) pore volume of the source i of binder.

The binder is advantageously a compound which is inert for the intended reaction (isomerizing dehydration of a primary alcohol). According to the invention, the binder is preferably a silicic binder, an $AlPO_4$, a clay, a zirconia, a Ti oxide, SiC, or mixtures thereof. Very preferably, it is a silicic binder.

The silicic binder preferably consists essentially of silica, meaning that the silicic binder consists of silica apart from the impurities, which have no catalytic effect. More particularly, said silica is an amorphous silica.

The silicic binder is composed advantageously of a silica source or of a mixture of silicas.

The binder content of the catalyst is between 10 and 45 wt %, preferably between 20 and 40 wt %.

Very advantageously, the catalyst consists of at least one zeolite having at least one series of channels, in which the aperture is of 8 oxygen atoms (8MR), and a silicic binder. Preferably, said catalyst consists of ferrierite zeolite and of silicic binder. Preferably, said catalyst consists of ferrierite zeolite and of silica, and in particular of amorphous silica.

Said catalyst is shaped (extruded) in a multilobate geometry.

Generally, the catalyst comprises no metals. According to the invention, this expression "no metals" means that there are no metals added during preparation. It is also understood that there may be impurities in the binders and thus in small amounts. In general, there is no aluminum or iron in the silica.

The process of the invention operates with a catalyst having a specific porosity, which gives it its performances. A linear relationship has been observed to exist between the pore volume and the amount of zeolite, this relationship being valid within a certain range, or given the different ranges, of pore volumes.

According to the invention, therefore, the catalyst has a porosity such that:
the average mesopore volume Vm is centered at plus or minus 20%, preferably plus or minus 15%, around the value defined by the formula $Vm=-0.004Tz+0.505$, the mesopores having a diameter of 3.6 nm to 50 nm,
the average macropore volume VM is centered at plus or minus 20%, preferably plus or minus 15%, around the value defined by the formula $VM=0.0101Tz-0.5375$, the macropores having a diameter of more than 50 nm and less than 7000 nm,
the average micropore volume Vµ is centered at plus or minus 20%, preferably plus or minus 15%, around the value defined by the formula $V\mu=0.0014Tz-0.0006$, the micropores having a diameter of less than 2 nm, and, in the formulas, Tz is expressed in wt % and the pore volumes are expressed in ml/g.

This catalyst also has an exposed geometric area of 2700 to 11 000 m$^2$/m$^3$ of catalyst bed volume, and preferably of 2800 to 9000 m$^2$/m$^3$.

Very advantageously, the catalyst consists of at least one zeolite having at least one series of channels, in which the aperture is of 8 oxygen atoms (8MR), and a silicic binder having a pore volume of between 0.5 and 0.9 ml/g. Preferably said catalyst consists of ferrierite zeolite and of silicic binder having a pore volume of between 0.5 and 0.9 ml/g. Advantageously said catalysts are trilobate or quadrilobate, and preferably quadrilobate.

Preferably, the silicic binder consists essentially of silica and the catalyst is quadrilobate, having a diameter relative to the circumscribed circle of between 1 mm and 5 mm, preferably between 1.2 and 3 mm. This catalyst preferably comprises no metals.

A catalyst having such morphological and textural characteristics thus makes it possible to improve the performances in isomerizing dehydration of a primary alcohol. A catalyst of this kind also exhibits enhanced stability with respect to deactivation. It is also able advantageously to operate in the absence of precoking.

Preparation Process

Said catalyst used in the process according to the invention is advantageously prepared according to a preparation process comprising at least the following steps:

a) a step for mixing at least one zeolite powder, preferably in proton or ammonium form, said zeolite having at least one series of channels having an aperture of 8 oxygen atoms (8MR), with at least one binder, preferably a silicic binder, as for example an amorphous silica powder, said zeolite representing between 55 and 90 wt % of the total weight of the mixture of zeolite and binder, said binder having a pore volume of between 0.5 and 0.9 ml/g;

b) a step for kneading the mixture obtained at the end of step a), in the presence of addition of solvent, advantageously of an aqueous solution, preferably water, and optionally of peptizing agent, until a pasty mixture is obtained;

c) a step for shaping of the pasty mixture obtained at the end of step b) into multilobate form, as for example by extrusion using a die of appropriate geometry;

d) a step for drying the shaped material obtained at the end of step c), advantageously at a temperature of between 50 and 200° C., preferably between 80 and 150° C., advantageously for a time of between 1 and 24 h, and advantageously under air;

e) an optional calcining step, at the end of step d) of drying the material, advantageously under dry air, at a temperature of from 400 to 800° C. and preferably for a period of from 2 to 12 h; and/or f) an optional step of heat treatment, at the end of the drying step d) or at the end of the optional calcining step e), at a temperature of between 500-700° C. under air, in the presence of 1 to 30 vol % of water in air, preferably 1% to 10%, advantageously for a time of from 1 to 4 hours.

The binder (and particularly the silicic binder) used in step a) is well known to the skilled person. The binder powder (and especially the silicic binder powder) makes a contribution to controlling the porosity of the final solid.

A source of silicic binder may be a precipitated silica or a silica derived from by-products such as fly ash, for example aluminosilicate or calcium silicate particles, and silica fume. It will be possible advantageously to use a colloidal silica, taking the form, for example, of a stabilized suspension.

The zeolite powder and the binder (such as silicic binder), preferably in powder form, are advantageously kneaded in the presence of a solvent (step b), preferably in the presence of an aqueous solution, and more preferably still in the presence of water, in which advantageously a peptizing agent may be dissolved in order to obtain better dispersion of the binder. The proportion of solvent, advantageously of aqueous solution, added is between 20 and 40 wt %, preferably between 25 and 35 wt %, and more preferably between 28 and 34 wt %, relative to the total weight of the mixture composed of the zeolite powder, the binder, the solvent, and optionally the peptizing agent. The consistency of the paste is adjusted by means of the amount of solvent. Adjusting the amount of solvent allows the loss on ignition of the paste to be modulated, and so makes it possible to obtain the desired geometric characteristics and the desired texturing properties for the final solid. The loss on ignition of the paste (or pasty mixture) obtained at the end of step b) in the preparation process according to the invention advantageously varies between 20% and 50%, preferably between 25% and 45%, and more preferably between 30% and 40%.

According to the invention, the loss on ignition (LOI) refers to the loss in mass experienced by a solid compound, a mixture of solid compounds or a paste during a heat treatment at 1000° C. for 2 hours, in a static oven (of muffle oven type), relative to the mass of the solid compound, of the mixture of solid compounds or of the paste in its initial form. The loss on ignition corresponds in general to the loss of solvent (such as water) present in the solids and originating from the solvent added to form the paste, but also to the removal of volatile organic compounds contained in the inorganic solid constituents.

The peptizing agent used optionally in step b) of the preparation process for the catalyst according to the invention may advantageously be an organic or inorganic acid or base, such as acetic acid, hydrochloric acid, sulfuric acid, formic acid, citric acid and nitric acid, alone or as a mixture, aqueous ammonia, an amine, a quaternary ammonium compound, selected from alkyl-ethanolamines or ethoxylated alkyl-amines, tetraethylammonium hydroxide (TEAOH) and tetramethylammonium.

In the shaping step c), the kneaded paste is extruded through a die whose geometry will impart the shape of the catalyst.

According to one embodiment of the invention, the process for preparing the catalyst may further comprise a step of "steaming", or heat treatment in steam, which is carried out at the end of the preparation process according to the invention, in other words after the drying step d) or after the optional calcining e) and/or heat treatment f) step(s) in the process for preparing the catalyst according to the invention. This optional steaming step, if it is integrated in the preparation process according to the invention, is carried out in steam, more particularly without an extraneous carrier gas, at a temperature of between 250 and 400° C., preferably between 300 and 350° C., at a pressure of more than 4 bar absolute (i.e., 0.4 MPa abs.) and preferably less than or equal to 15 bar absolute (i.e., 1.5 MPa abs.), and with an injected water input corresponding to the hourly mass of water relative to the mass of catalyst (WWH) of between 3 and 9 h$^{-1}$, preferably of between 5 and 7 h$^{-1}$.

The examples that follow are presented as nonlimiting illustrations of the treatment process according to the invention.

EXAMPLES

In the examples, the pore volumes were measured by the methods of mercury intrusion porosimetry and nitrogen adsorption isotherm, which have been described above in the present text, hence explaining the differences relative to the volumes calculated according to the formulas given, but remaining within a difference interval of 20%.

Example 1 (According to the Invention)

Catalyst A is prepared by kneading together 70 wt % of commercial ferrierite in ammonium form having an Si/Al atomic ratio of 20, 9 wt % of a silica source in powder form with a pore volume of 1.54 ml/g, and 21 wt % of a silica source in powder form with a pore volume of 0.312 ml/g. The binder used for preparing catalyst A is a silicic binder in powder form, composed of 30 wt % of the silica source with a pore volume of 1.54 ml/g and 70 wt % of the silica source with a pore volume of 0.312 ml/g. The binder has a resultant total pore volume of Vp(binder)=0.680 ml/g. It represents 30 wt % of the powder mixture of ferrierite zeolite+silicas. The two silica powders are mixed with the zeolite. A basic aqueous solution containing TEAOH (tetraethylammonium hydroxide) is subsequently added to the mixture of powders, which is then kneaded to form a paste, in such a way that: the TEAOH content of the zeolite+silicas powder mixture is 2.5 wt % and the LOI of the resultant paste is 37%. The solid was extruded in quadrilobate form with a diameter of 1.6 mm, dried at 80° C. for 12 h, and then calcined in humid air (6% v/v, volume of water relative to the volume of complete gaseous effluent) at 600° C. for 2 h.

The catalyst A obtained has a $S_{BET}$ specific surface area of 300 m²/g, a mesopore volume 0.24 ml/g, a macropore volume of 0.16 ml/g and a micropore volume of 0.097 ml/g. The calculated exposed geometric surface area is 3404 m2/m3, for a void level in the catalyst bed of 38.5% and an average length of 3.5 mm.

Example 2 (Comparative)

Catalyst B is prepared by kneading together 70 wt % of commercial ferrierite in ammonium form having an Si/Al atomic ratio of 20, and 30 wt % of a silica source in powder form having a pore volume of 0.312 ml/g. The silicic binder is mixed with the zeolite. A basic aqueous solution containing TEAOH is added to the mixture of powders, which is then kneaded to form a paste, in such a way that: the TEAOH content of the zeolite+silicas powder mixture is 2.5 wt % and the LOI of the resultant paste is 34%. The solid was extruded in cylinder form with a diameter of 2.1 mm, dried at 80° C. for 12 h, and then calcined in humid air (6% v/v, volume of water relative to the volume of complete gaseous effluent) at 600° C. for 2 h.

The catalyst B obtained has a $S_{BET}$ specific surface area of 280 m²/g, a mesopore volume of 0.14 ml/g, a macropore volume of 0.21 ml/g and a micropore volume of 0.094 ml/g. The calculated exposed geometric surface area is 1535 m2/m3, for a void level in the catalyst bed of 38.5% and an average length of 3.5 mm.

Example 3 (Comparative)

Catalyst C is prepared by kneading together 70 wt % of commercial ferrierite in ammonium form having an Si/Al atomic ratio of 20, and 30 wt % of a silica source in powder form having a pore volume of 0.312 ml/g. The silicic binder and the zeolite are mixed. A basic aqueous solution containing TEAOH is added to the mixture of powders, which is then kneaded to form a paste, in such a way that: the TEAOH content of the zeolite+silica powders mixture is 2.5 wt % and the LOI of the resultant paste is 35.5%. The solid was extruded in trilobate form with a diameter of 2.1 mm, dried at 80° C. for 12 h, and then calcined in humid air (6% v/v, volume of water relative to the volume of complete gaseous effluent) at 600° C. for 2 h.

The catalyst C obtained has a $S_{BET}$ specific surface area of 333 m²/g, a mesopore volume of 0.15 ml/g, a macropore volume of 0.13 ml/g and a micropore volume of 0.102 ml/g. The calculated exposed geometric surface area is 2270 m2/m3, for a void level in the catalyst bed of 38.5% and an average length of 3.5 mm.

Example 4 (According to the Invention)

Catalyst D is prepared by kneading together 70 wt % of commercial ferrierite in ammonium form having an Si/Al atomic ratio of 20, 11 wt % of a silica source with a pore volume of 1.54 ml/g, and 19 wt % of a silica source with a pore volume of 0.312 ml/g. The binder used for preparing catalyst D is thus a silicic binder in powder form, composed of approximately 36.7 wt % of the silica source with a pore volume of 1.54 ml/g and 63.3 wt % of the silica source with a pore volume of 0.312 ml/g. The binder has a resultant total pore volume of Vp(binder)=0.762 ml/g. It represents 30 wt % of the powder mixture of ferrierite zeolite+silicas. The two silica powders are mixed with the zeolite. A basic aqueous solution containing TEAOH (tetraethylammonium hydroxide) is subsequently added to the mixture of powders, which is then kneaded to form a paste, in such a way that: the TEAOH content of the zeolite+silicas powder mixture is 2.5 wt % and the LOI of the resultant paste is 35.5%. The solid was extruded in trilobate form with a diameter of 1.6 mm, dried at 80° C. for 12 h, and then calcined in humid air (6% v/v, volume of water relative to the volume of complete gaseous effluent) at 600° C. for 2 h.

The catalyst D obtained has a $S_{BET}$ specific surface area of 341 m²/g, a mesopore volume of 0.19 ml/g, a macropore volume of 0.19 ml/g and a micropore volume of 0.101 ml/g. The calculated exposed geometric surface area is 2871 m2/m3, for a void level in the catalyst bed of 38.5% and an average length of 3.5 mm.

Example 5 (Comparative)

Catalyst E is prepared by kneading together 70 wt % of commercial ferrierite in ammonium form having an Si/Al atomic ratio of 20 and 30 wt % of silica having a pore volume of 0.377 ml/g. The silica is mixed into the zeolite. A basic aqueous solution containing TEAOH is added and the mixture is kneaded to form a paste. The addition of the aqueous solution is such that the TEAOH (tetraethylammonium hydroxide) content of the zeolite+silica powder mixture is 2.5 wt % and the LOI of the resulting paste is 33%. The solid was extruded in quadrilobate form with a diameter of 1.6 mm, dried at 80° C. for 12 h, and then calcined in humid air (6% v/v, volume of water relative to the volume of complete gaseous effluent) at 600° C. for 2 h.

The catalyst E obtained has a $S_{BET}$ specific surface area of 326 m²/g, a mesopore volume of 0.17 ml/g, a macropore volume of 0.27 ml/g and a micropore volume of 0.097 ml/g. The calculated exposed geometric surface area is 3404 m2/m3, for a void level in the catalyst bed of 38.5% and an average length of 3.5 mm.

Example 6: Catalytic Testing: Dehydration of a Single-Phase Isobutanol/Water Feedstock in the Presence of Catalysts A, B, C, D and E The dehydration step is performed in a catalytic test unit comprising a fixed bed operating in downflow mode. The catalyst is loaded into a 316 L stainless-steel reactor having an internal diameter of 13 mm. The catalyst is subsequently activated at 450° C. under 6 l/h of air for a stage of one hour after a temperature increase of 10° C./min. The temperature is then lowered to the test temperature under 6 l/h of nitrogen in order to remove the air present in the system before injection of the alcohol feedstock.

The feedstock is vaporized in lines heated at 150-180° C. upstream of the reactor, then injected into the catalytic reactor. The operating conditions are as follow: weighted average temperature of 300° C., WWH (weight of feedstock per weight of catalyst per gram) of 7 $h^{-1}$ for 24 h, then 12 $h^{-1}$ for 48 h, then 20 $h^{-1}$ for 72 h, then again WWH 7 $h^{-1}$ for 24 h (return point).

The analysis of the total effluent is carried out at the reactor outlet on an in-line gas chromatograph equipped with two columns, so making it possible to determine the conversion of isobutanol, the selectivities for various products and, in particular, the selectivity for butenes, and the fraction of linear butenes in the butene cut, this being the fraction to be maximized. The analyzer also makes it possible to measure the selectivity for secondary products such as propene or products containing five or more carbon atoms. The measurement of the average conversion reached during the 24 h of the return point is compared to the average conversion during the first 24 hours at WWH of 7 $h^{-1}$, and makes it possible to evaluate the loss of activity during the test. By determining the deactivation gradient on the plot of conversion of the monoalcohol at WWH of 20 $h^{-1}$, it is possible to evaluate and compare the stability of the catalysts under deactivating conditions. It is expressed in loss of % alcohol converted per hour.

The results obtained are shown in the table below.

catalyst comprising at least one zeolite having at least one series of channels having an aperture of 8 oxygen atoms (8MR) and being of structural type FER, the catalyst being trilobate or quadrilobate and having an average mesopore volume Vm centered at plus or minus 20% around the value defined by the formula Vm=−0.004Tz+0.505, the mesopores having a diameter of 3.6 nm to 50 nm, an average macropore volume VM centered at plus or minus 20% around the value defined by the formula VM=0.0101Tz−0.5375, the macropores having a diameter of more than 50 nm and less than 7000 nm, an average micropore volume Vμ centered at plus or minus 20% around the value defined by the formula Vμ=0.0014Tz−0.0006, the micropores having a diameter of less than 2 nm, and, in the formulas, Tz is expressed in wt % and the pore volumes are expressed in ml/g, an exposed geometric area of 2700 to 11,000 $m^2/m^3$ of catalyst bed volume, the exposed geometric area being the geometric surface area of a catalyst bed expressed relative to the volume occupied by the same catalyst bed.

2. The catalyst as claimed in claim 1, wherein the zeolite is ferrierite, FU-9, ISI-6, NU-23, ZSM-35, or mixtures thereof.

3. The catalyst as claimed in claim 1, wherein the zeolite is ferrierite.

4. The catalyst as claimed in claim 1, wherein the zeolite content is between 55 and 80 wt % relative to the total weight of said catalyst.

5. The catalyst as claimed in claim 1, wherein the binder is selected from the group consisting of a silicic binder, an AlPO4, a clay, a zirconia, a Ti oxide, and SiC.

6. The catalyst as claimed in claim 1, wherein the binder is a silicic binder.

7. The catalyst as claimed in claim 1, wherein the pore volume of the binder before preparation is between 0.6 and 0.8 ml/g.

| | Salt C4 = at the return point (%) | Initial conversion of isobutanol at wwh 7 h−1 (%) | % of linear butenes in the C4 olefins at the return point | Deactivation gradient of wwh 20 $h^{-1}$ (% conversion/h) | Loss of conversion at the return point (% absolute) | Exposed geometric surface area ($m^2/m^3$) |
|---|---|---|---|---|---|---|
| Catalyst A (compliant) Quadrilobate D = 1.6 mm | 98.6 | 100 | 82.4 | −0.0307 | 0.05 | 3404 |
| Catalyst B (non compliant) Cylinder D = 2.1 mm | 98.5 | 100 | 82.3 | −0.232 | 5.66 | 1535 |
| Catalyst C (non compliant) trilobate D = 2.1 mm | 98.9 | 100 | 82.2 | −0.201 | 6.10 | 2270 |
| Catalyst D (compliant) Trilobate D = 1.6 mm | 98.7 | 100 | 81.5 | −0.060 | 0.05 | 2871 |
| Catalyst E (non compliant) quadrilobate D = 1.6 mm | 98.6 | 100 | 81.0 | −0.075 | 0.1 | 3404 |

Catalysts A and D according to the invention exhibit a deactivation of about zero at the return point, and their deactivation rate is lower under high WWH conditions than that of the catalysts B, C, and E. Their stability is therefore improved relative to the catalysts B, C, and E. Their selectivity for linear butenes is improved.

The invention claimed is:

1. A catalyst comprising at least one zeolite and at least one binder, in which the amount by weight Tz of zeolite is 55-90 wt %, and the binder content is 10-45 wt % relative to the total weight of said catalyst, said binder having a pore volume before preparation of between 0.5 and 0.9 ml/g, said

8. The catalyst as claimed in claim 1, wherein the binder content is between 20 and 40 wt %, relative to the total weight of said catalyst.

9. The catalyst as claimed in claim 1, wherein the catalyst is quadrilobate and has a diameter relative to a circumscribed circle of between 1 mm and 9 mm.

10. The catalyst as claimed in claim 1, wherein the binder is a silicic binder, the catalyst being quadrilobate, having a diameter relative to a circumscribed circle of between 1.2 and 2 mm, and the exposed geometric surface is between 2800 and 9000 $m^2/m^3$.

11. The catalyst as claimed in claim 1, comprising no added metals.

12. The catalyst as claimed in claim 1, which catalyst is trilobate.

13. The catalyst as claimed in claim 1, which catalyst is quadrilobate.

14. The catalyst as claimed in claim 1, wherein the zeolite is a ferrierite, and has an Si/Al molar ratio=15 to 70.

15. The catalyst as claimed in claim 1, wherein the binder consists essentially of silica.

16. The catalyst as claimed in claim 1, wherein the catalyst is quadrilobate and has a diameter relative to a circumscribed circle of between 1.2 and 2 mm.

17. A process for preparing the catalyst as claimed in claim 1, comprising at least the following:
- a) mixing at least one zeolite powder, said zeolite having at least one series of channels having an aperture of 8 oxygen atoms (8MR) and being of structural type FER, with at least one binder, said zeolite representing between 55 and 90 wt % of the total weight of the mixture of zeolite and binder, said binder having a pore volume of between 0.5 and 0.9 ml/g,
- b) kneading the mixture obtained at the end of a), in the presence of addition of solvent, and optionally of peptizing agent, until a pasty mixture is obtained;
- c) multilobate shaping of the pasty mixture obtained at the end of b), d) drying the shaped material obtained at the end of c),
- e) optionally calcining of the shaped material, at the end of d) of drying the material, and/or
- f) optionally heat treatment of the shaped material, at the end of d) drying of the material or at the end of the optional calcining e), in the presence of 1 to 30 vol % of water in air.

18. The catalyst preparation process as claimed in claim 17, further comprising steaming carried out after the drying d) or after the optional calcining e) and/or heat treatment f), in steam, at a temperature of between 250 and 400° C., at a pressure of more than 4 bar absolute and with an injected water input corresponding to the hourly mass of water relative to the mass of catalyst (WWH) of between 3 and 9 $h^{-1}$.

19. A process for isomerizing dehydration of a feedstock comprising, alone or in a mixture, a primary monoalcohol of formula R—$CH_2$—OH, in which R is a nonlinear alkyl radical of general formula $C_nH_{2n+1}$ where n is an integer of between 3 and 20, said process comprising a step of isomerizing dehydration operated in the gas phase at a weighted average temperature of between 250 and 460° C., at a pressure of between 0.2 MPa and 1 MPa, at a weight hourly space velocity (WWH) of between 1 and 25 $h^{-1}$, in the presence of a catalyst comprising at least one zeolite and at least one binder, in which the amount by weight Tz of zeolite is 55-90 wt % and the binder content is 10-45 wt % relative to the total weight of said catalyst and in which said zeolite has at least one series of channels with an aperture of 8 oxygen atoms (8MR) and being of structural type FER, said binder having a pore volume before preparation of between 0.5 and 0.9 ml/g, the catalyst being trilobate or quadrilobate and having

- an average mesopore volume Vm centered at plus or minus 20% around the value defined by the formula Vm=−0.004Tz+0.505, the mesopores having a diameter of 3.6 nm to 50 nm,
- an average macropore volume VM centered at plus or minus 20% around the value defined by the formula VM=0.0101Tz−0.5375, the macropores having a diameter of more than 50 nm and less than 7000 nm,
- an average micropore volume Vμ centered at plus or minus 20% around the value defined by the formula Vμ=0.0014Tz−0.0006, the micropores having a diameter of less than 2 nm, and, in the formulas, Tz is expressed in wt % and the pore volumes are expressed in ml/g,

- an exposed geometric area of 2700 to 11,000 $m^2/m^3$ of catalyst bed volume, the exposed geometric area being the geometric surface area of a catalyst bed expressed relative to the volume occupied by the same catalyst bed.

20. The process as claimed in claim 19, wherein the catalyst comprises no added metals.

21. The process as claimed in claim 19, wherein said monoalcohol is isobutanol.

22. The process as claimed in claim 19, wherein the feedstock comprises from 40 to 100 wt % of said primary monoalcohol.

* * * * *